(12) United States Patent
Messerschmidt

(10) Patent No.: US 11,445,953 B2
(45) Date of Patent: Sep. 20, 2022

(54) COMBINATION BLOOD LANCET AND ANALYZER

(71) Applicant: NUEON INC., Menlo Park, CA (US)

(72) Inventor: Robert G. Messerschmidt, Menlo Park, CA (US)

(73) Assignee: NUEON INC., Menlo Park, CA (US)

( * ) Notice: Subject to any disclaimer, the term of this patent is extended or adjusted under 35 U.S.C. 154(b) by 196 days.

(21) Appl. No.: 16/404,564

(22) Filed: May 6, 2019

(65) Prior Publication Data

US 2019/0269358 A1    Sep. 5, 2019

Related U.S. Application Data

(63) Continuation of application No. PCT/US2017/060007, filed on Nov. 3, 2017.

(60) Provisional application No. 62/417,838, filed on Nov. 4, 2016.

(51) Int. Cl.
*A61B 5/15* (2006.01)
*A61B 5/151* (2006.01)
*A61B 5/157* (2006.01)
*A61B 5/00* (2006.01)

(52) U.S. Cl.
CPC ........ *A61B 5/150022* (2013.01); *A61B 5/157* (2013.01); *A61B 5/15105* (2013.01); *A61B 5/15142* (2013.01); *A61B 5/150427* (2013.01); *A61B 5/0075* (2013.01); *A61B 5/150862* (2013.01)

(58) Field of Classification Search
None
See application file for complete search history.

(56) References Cited

U.S. PATENT DOCUMENTS

| | | | |
|---|---|---|---|
| 4,427,889 A * | 1/1984 | Muller | G01N 33/66 250/339.11 |
| 4,514,050 A | 4/1985 | Stites | |
| 4,775,637 A | 10/1988 | Sutherland | |
| 4,882,492 A | 11/1989 | Schlager | |
| 5,200,609 A | 4/1993 | Sting | |
| 5,280,786 A | 1/1994 | Wlodarczyk | |
| 5,288,646 A | 2/1994 | Lundsgaard | |
| 5,327,777 A | 7/1994 | Kaye | |
| 5,331,958 A | 7/1994 | Oppenheimer | |
| 5,362,445 A | 11/1994 | Miyahara | |

(Continued)

FOREIGN PATENT DOCUMENTS

| | | |
|---|---|---|
| EP | 0476192 | 3/1992 |
| EP | 2700933 | 2/2014 |

(Continued)

OTHER PUBLICATIONS

Alam, "Measurement of pH in Whole Blood by Near-infrared Spectroscopy", Applied Spectroscopy, Mar. 1, 1999, pp. 316-324, vol. 53, issue 3—Abstract.

(Continued)

*Primary Examiner* — Rufus L Phillips
(74) *Attorney, Agent, or Firm* — FisherBroyles LLP; John Shimmick

(57) ABSTRACT

Methods and systems for collecting and analyzing blood are provided. The methods and systems generally operate by collecting a blood sample on a portion of a lancet and subjecting the blood sample to optical spectroscopy.

16 Claims, 9 Drawing Sheets

(56) References Cited

U.S. PATENT DOCUMENTS

| | | |
|---|---|---|
| 5,366,903 A | 11/1994 | Lundsgaard |
| 5,437,840 A | 8/1995 | King |
| 5,525,518 A | 6/1996 | Lundsgaard |
| 5,599,959 A | 2/1997 | Hosmane |
| 5,636,633 A * | 6/1997 | Messerschmidt .... G01N 21/4738 250/341.8 |
| 5,636,640 A | 6/1997 | Staehlin |
| 5,689,333 A | 11/1997 | Batchelder |
| 5,706,208 A | 1/1998 | Osten |
| 5,729,333 A | 3/1998 | Osten |
| 5,830,133 A | 11/1998 | Osten |
| 6,006,119 A | 12/1999 | Soller |
| 6,141,100 A | 10/2000 | Burka |
| 6,266,139 B1 | 7/2001 | Mannhardt |
| 6,285,448 B1 | 9/2001 | Kuenstner |
| 6,341,257 B1 * | 1/2002 | Haaland .................. G01J 3/28 702/22 |
| 6,353,471 B1 | 3/2002 | Samsoondar |
| 6,383,179 B1 | 5/2002 | Neuberger |
| 6,603,987 B2 | 8/2003 | Whitson |
| 6,614,730 B1 | 9/2003 | Vo-Dinh |
| 6,638,769 B2 | 10/2003 | Lilja |
| 6,676,903 B2 | 1/2004 | Potyrailo |
| 6,788,394 B1 | 9/2004 | Garcia-Rubio |
| 6,791,674 B2 | 9/2004 | Kawano |
| 6,866,675 B2 | 3/2005 | Perez |
| 6,944,487 B2 | 9/2005 | Maynard |
| 7,001,344 B2 | 2/2006 | Freeman |
| 7,004,928 B2 | 2/2006 | Aceti |
| 7,150,755 B2 | 12/2006 | LeVaughn |
| 7,271,912 B2 | 9/2007 | Sterling |
| 7,282,105 B1 | 10/2007 | Plunkett |
| 7,291,497 B2 | 11/2007 | Holmes |
| 7,299,711 B1 | 11/2007 | Linker |
| 7,319,894 B2 | 1/2008 | Higgins |
| 7,426,407 B2 | 9/2008 | Higgins |
| 7,570,357 B2 | 8/2009 | Tsenkova |
| 7,593,108 B2 | 9/2009 | Sterling |
| 7,656,523 B2 | 2/2010 | Sun |
| 7,787,109 B2 | 8/2010 | Dosmann |
| 7,869,009 B2 | 1/2011 | Dosmann |
| 7,969,307 B2 | 6/2011 | Peeters |
| 8,033,898 B2 | 10/2011 | McNaughton et al. |
| 8,041,538 B2 | 10/2011 | Meyer |
| 8,077,042 B2 | 12/2011 | Peeters |
| 8,160,665 B2 | 4/2012 | Mischler |
| 8,184,273 B2 | 5/2012 | Dosmann |
| 8,206,650 B2 | 6/2012 | Samsoondar |
| 8,303,518 B2 | 11/2012 | Aceti |
| 8,483,789 B2 | 7/2013 | Higgins |
| 8,690,798 B2 | 4/2014 | Douglas |
| 8,808,202 B2 | 8/2014 | Brancazio |
| 8,821,412 B2 | 9/2014 | Gonzalez-Zugasti |
| 8,821,413 B2 | 9/2014 | Effenhauser |
| 8,830,449 B1 | 9/2014 | Lamego |
| 8,900,514 B2 | 12/2014 | Forsell |
| 9,113,836 B2 | 8/2015 | Bernstein |
| 9,133,024 B2 | 9/2015 | Phan |
| 9,217,706 B2 | 12/2015 | Mucci |
| 9,259,175 B2 | 2/2016 | Stafford |
| 9,291,504 B2 | 3/2016 | Goldring |
| 9,341,515 B2 | 5/2016 | Schulte |
| 9,377,396 B2 | 6/2016 | Goldring et al. |
| 9,470,673 B2 | 10/2016 | Samsoondar |
| 9,470,699 B2 | 10/2016 | Peeters |
| 9,603,562 B2 | 3/2017 | Aceti |
| 10,337,984 B2 | 7/2019 | Messerschmidt |
| 2002/0042594 A1 * | 4/2002 | Lum .................. A61B 18/14 604/117 |
| 2002/0122168 A1 | 9/2002 | Grcia-Rubio |
| 2002/0123677 A1 | 9/2002 | Miki |
| 2002/0156380 A1 | 10/2002 | Feld |
| 2003/0018282 A1 | 1/2003 | Effenhauser |
| 2003/0059948 A1 | 3/2003 | Hildenbrand |
| 2003/0083686 A1 | 5/2003 | Freeman |
| 2003/0171696 A1 | 9/2003 | Dosmann |
| 2003/0175160 A1 | 9/2003 | Archibald |
| 2003/0189707 A1 | 10/2003 | Naya |
| 2003/0227628 A1 | 12/2003 | Kreimer |
| 2004/0186359 A1 | 9/2004 | Beaudoin |
| 2005/0208501 A1 | 9/2005 | Goldrick |
| 2005/0244952 A1 | 11/2005 | Cohen |
| 2006/0043301 A1 | 3/2006 | Mantele |
| 2006/0057554 A1 | 3/2006 | Watling |
| 2006/0057642 A1 | 3/2006 | Kiefer |
| 2006/0074282 A1 | 4/2006 | Ward |
| 2006/0135861 A1 | 6/2006 | Lucassen |
| 2006/0135917 A1 * | 6/2006 | Reihl .................. A61B 5/14528 604/272 |
| 2006/0166302 A1 | 7/2006 | Clarke |
| 2007/0076208 A1 | 4/2007 | Koo |
| 2007/0134738 A1 | 6/2007 | Wells |
| 2007/0213636 A1 | 9/2007 | Kuriger |
| 2008/0036999 A1 * | 2/2008 | Petrich .................. A61B 5/0059 356/39 |
| 2008/0138793 A1 | 6/2008 | Lindberg |
| 2008/0153171 A1 | 6/2008 | Liu |
| 2008/0154217 A1 * | 6/2008 | Carrez .................. A61L 27/50 604/272 |
| 2008/0218734 A1 | 9/2008 | Higashi |
| 2008/0218736 A1 | 9/2008 | Shaw |
| 2008/0300508 A1 | 12/2008 | Tomer |
| 2009/0041924 A1 * | 2/2009 | Steube .............. A61B 17/3421 427/2.28 |
| 2010/0105098 A1 | 4/2010 | Frederiske |
| 2010/0121163 A1 | 5/2010 | Vestel |
| 2010/0129919 A1 | 5/2010 | Levin |
| 2010/0142773 A1 | 6/2010 | Cha |
| 2010/0196945 A1 | 8/2010 | Forsell |
| 2010/0245803 A1 | 9/2010 | Samsoondar |
| 2010/0256524 A1 | 10/2010 | Levinson |
| 2010/0284004 A1 | 11/2010 | Reich |
| 2011/0003707 A1 | 1/2011 | Goix |
| 2011/0009738 A1 * | 1/2011 | Zemel ................ A61B 5/15003 600/424 |
| 2011/0020849 A1 | 1/2011 | Spence |
| 2011/0105952 A1 | 5/2011 | Bernstein |
| 2011/0111435 A1 | 5/2011 | Dobson |
| 2011/0143961 A1 * | 6/2011 | Lednev .................. G01N 21/65 506/13 |
| 2011/0144463 A1 | 6/2011 | Pesach |
| 2011/0172508 A1 | 7/2011 | Chickering |
| 2011/0196239 A1 | 8/2011 | Behrend |
| 2011/0223654 A1 | 9/2011 | Holman |
| 2011/0278472 A1 | 11/2011 | Atzler |
| 2011/0287948 A1 | 11/2011 | Suresh |
| 2012/0016818 A1 | 1/2012 | Hackett |
| 2012/0142559 A1 | 6/2012 | Tuytten |
| 2012/0205727 A1 | 8/2012 | Kanakasabapathy |
| 2012/0257199 A1 | 10/2012 | Liu |
| 2012/0261256 A1 | 10/2012 | Chang |
| 2012/0271125 A1 | 10/2012 | Bernstein |
| 2012/0274934 A1 | 11/2012 | Messerschmidt |
| 2013/0143226 A1 * | 6/2013 | Hill .................. A61B 5/15117 435/6.12 |
| 2013/0338013 A1 | 12/2013 | Zhong |
| 2014/0100524 A1 * | 4/2014 | Zarei Mahmoodabadi ................ A61B 5/489 604/116 |
| 2014/0112568 A1 | 4/2014 | Liu |
| 2014/0148669 A1 | 5/2014 | Saban |
| 2014/0276217 A1 * | 9/2014 | Liepold ............ A61B 5/150305 600/573 |
| 2014/0336534 A1 | 11/2014 | Balligand |
| 2014/0336536 A1 | 11/2014 | Brancazio |
| 2014/0339428 A1 * | 11/2014 | O'Brien ............... G01N 21/359 250/339.07 |
| 2015/0055121 A1 | 2/2015 | Forsell |
| 2015/0057530 A1 | 2/2015 | Roggeveen |
| 2015/0061876 A1 * | 3/2015 | Chang ............... A61M 5/16845 340/613 |
| 2015/0087944 A1 | 3/2015 | Levinson |
| 2015/0208985 A1 | 7/2015 | Huang |

(56) References Cited

U.S. PATENT DOCUMENTS

| | | | |
|---|---|---|---|
| 2015/0338338 | A1 | 11/2015 | Messerschmidt |
| 2016/0025624 | A1 | 1/2016 | Mucci |
| 2016/0029937 | A1 | 2/2016 | Sia |
| 2016/0058354 | A1 | 3/2016 | Phan |
| 2016/0066828 | A1 | 3/2016 | Phan |
| 2016/0123869 | A1 | 5/2016 | Messerschmidt |
| 2016/0143539 | A1* | 5/2016 | Koerner ............... G01J 3/0213 600/427 |
| 2016/0151569 | A1 | 6/2016 | Stafford |
| 2016/0302707 | A1 | 10/2016 | Pesach |
| 2017/0010154 | A1 | 1/2017 | Spudich |
| 2017/0127990 | A1 | 5/2017 | Levinson |
| 2017/0138845 | A1* | 5/2017 | Birarda ............. G01N 15/1463 |
| 2017/0350814 | A1 | 12/2017 | Messerschmidt |
| 2018/0136193 | A1 | 5/2018 | Messerschmidt |

FOREIGN PATENT DOCUMENTS

| | | | |
|---|---|---|---|
| EP | 3282937 | A1 | 2/2018 |
| GB | 740181 | A | 11/1955 |
| JP | 2002131319 | | 5/2002 |
| WO | 1986000513 | | 1/1986 |
| WO | 02058556 | | 8/2002 |
| WO | 03055379 | A2 | 7/2003 |
| WO | 2005080946 | | 9/2005 |
| WO | 2009117416 | | 9/2009 |
| WO | 2011153271 | A1 | 12/2011 |
| WO | 2013058084 | | 4/2013 |
| WO | 2013134786 | A2 | 9/2013 |
| WO | 2013155458 | A1 | 10/2013 |
| WO | 2013156806 | A2 | 10/2013 |
| WO | 2013180652 | A1 | 12/2013 |
| WO | 2013186628 | | 12/2013 |
| WO | 2014191980 | | 12/2014 |
| WO | 2015009970 | A1 | 1/2015 |
| WO | 2015112919 | | 7/2015 |
| WO | 2015131151 | A2 | 9/2015 |
| WO | 2015166237 | A1 | 11/2015 |
| WO | 2015179288 | A1 | 11/2015 |
| WO | 2015179969 | | 12/2015 |
| WO | 2016086071 | A1 | 6/2016 |
| WO | 2016168090 | A1 | 10/2016 |
| WO | 2017165403 | A1 | 9/2017 |
| WO | 2018085699 | A1 | 5/2018 |

OTHER PUBLICATIONS

Bo, "Capillary method for measuring near-infrared spectra of microlitre volume liquids", Journal of Zhejiang University-3CIENCE A, Feb. 1, 2007, pp. 171-175, vol. 8, Issue 2—Abstract.

Domjan, "Rapid Analysis of Whole Blood and Blood Serum Using near Infrared Spectroscopy", Journal of Near infrared Spectroscopy, Mar. 1, 1994, pp. 67-78, vol. 2, Issue 2—Abstract.

Eigenvector Research Incorporated website. Accessed Apr. 30, 2015. http://www.eigenvector.com/software/solo.htm.

Engel, "Seventh Sense Biosystems Sucks in $10M for Simple Blood-Draw Device", Xconomy Boston, Nov. 18, 2016, http://www.xconomy.com/boston/2016/11/18/seventh-sense-biosystems-sucks-in-10m-for-simple-blood-draw-device/#.

Giardina et al., "The Multiple Functions of Hemoglobin", Critical Reviews in Biochemistry and Molecular Biology, (Mar. 1, 1995), vol. 30, pp. 165-196, XP 055498007.

Huang, "Optimal waveband and mathematical model for analysis of human whole blood glucose by near infrared transmission spectroscopy", 5th International Symposium on Advanced Optical Manufacturing and Testing Technologies, Oct. 11, 2010, Dalian, China—Abstract.

International Preliminary Report on Patentability for corresponding International Application No. PCT/US2017/060007, 8 pages (dated May 16, 2019).

International Search Report and Written Opinion for corresponding International Application No. PCT/US2017/060007, 10 pages (dated Apr. 5, 2018).

Kim, "Prediction of glucose in whole blood by near-infrared spectroscopy: Influence of wavelength region, preprocessing, and hemoglobin concentration", Journal of Biomedical Optics, Jul. 1, 2006, 11(4), 041128—Abstract.

Lafrance, "Measurement of lactate in whole human blood with near-infrared transmission spectroscopy", Talanta, Jul. 4, 2003, pp. 635-641, vol. 60, Issue 4, Elsevier—Abstract.

Lakshmi et al., "A simple slide test to assess erythrocyte aggregation in acute ST-elevated myocardial infarction and acute ischemic stroke: Its prognostic significance", Journal of Pathology and Microbiology, (Jan. 1, 2011), vol. 54, pp. 63-69, XP009507350.

Liu et al. "Application of a Genetic Algorithm to Quantitative Analysis of Overlapped FTIR Spectra", Spectroscopy Letters, vol. 34, No. 1, Jan. 22, 2001.

Murayama, "Near-infrared spectroscopy for liquids of microliter volume using capillaries with wall transmission", Analyst, 2003, Issue 7—Abstract.

Staniszewska-Slezak et al. "Plasma biomarkers of pulmonary hypertension identified by Fourier transform infrared spectroscopy and principal component analysis", The Analyst, vol. 140, No. 7, Jan. 1, 2015.

Sund et al. "Cell Membrane Orientation Visualized by Polarized Total Internal Reflection by polarized total internal reflection fluorescence," Biophysical Journal, vol. 77. Issue 4, Oct. 1999, pp. 2266-2283.

Turza, "Near Infrared Analysis of Whole Blood and Plasma in Blood-Collecting Tubes", Journal of Near Infrared Spectroscopy, Jun. 1, 2006, pp. 147-153, vol. 14, issue 3—Abstract.

Wan X, "identification of Animal Whole Blood Based on Near Infrared Transmission Spectroscopy", PubMed, Guang Pu Xue Yu Guang Pu Fen Xi. Jan. 2016; 36(1):80-3. Chinese—Abstract.

* cited by examiner

COMBINATION BLOOD LANCET AND ANALYZER

CROSS-REFERENCE

The present application claims priority to PCT/US2017/060007, filed Nov. 3, 2017, entitled "COMBINATION BLOOD LANCET AND ANALYZER" which claims priority to U.S. Provisional Application Ser. No. 62/417,838, filed on Nov. 4, 2016, entitled "COMBINATION BLOOD LANCET AND ANALYSIS MEANS", which applications are incorporated herein by reference in their entirety for all purposes.

BACKGROUND

The field of the present invention is related to biomarkers of health, and more specifically to one or more of detecting, diagnosing, screening, tracking over time, or ruling out, one or more conditions such as high blood pressure and the harmful cardiovascular effects of high blood pressure. Examples of harmful effects of high blood pressure can include one or more of inflammation, coronary artery disease, stable plaques, unstable plaques, or other vascular factors related to the onset of heart disease and heart attack in humans.

Prior methods and apparatus of measuring biomarkers are less than ideal in at least some respects. Prior methods and apparatus of measuring blood pressure and diagnosing subjects can be less than ideal in at least some instances. Although blood pressure measurements can be used to assess the health of a subject and guide treatment, the prior methods and apparatus can be less than ideal. Blood pressure measurements based on the sphygmomanometer, also referred to as a blood pressure cuff, can have problems and deficiencies in at least some instances. For example, blood pressure cuff measurements can result in less than ideal measurements that may be related to one or more of the following: observer error; systematic intraobserver and interobserver errors; terminal digit preference, rounding to favorite digit; observer prejudice; white coat hypertension (high only in doctor's office); masked hypertension (normal in office, high at other times of day); instrument error; defective control valve; improper fit of cuff, too large or too small; inadequate length of tubing; connections not airtight; position of manometer causes reading error; placement of cuff error; diastolic dilemma (muffling of sounds can occur 10 mm before complete disappearance); two arms exhibiting different readings; deflation too rapid. These errors can lead to inaccurate blood pressure readings that may be related to improper diagnoses in at least some instances. For example, errors as large as 20 mm Hg may occur in at least some instances.

If a subject is incorrectly diagnosed as having high blood pressure when actually having low blood pressure, this person may be placed on a daily blood pressure medication. Many of these medications may have side effects, and more people than would be ideal can be subjected to the side effects of blood pressure medications. Also, blood pressure measurement errors may result in a person who actually has high blood pressure being misdiagnosed as having low blood pressure. An incorrect diagnosis for a subject with high blood pressure can result in that subject not receiving appropriate medication, such that the high blood pressure may not be untreated in at least some instances. Inappropriate management of high blood pressure can result in injury to the subject and may even be fatal in at least some instances, and it would be helpful to have fewer misdiagnoses of high blood pressure.

Work in relation to embodiments suggest that it would desirable to have a record of blood pressure and of cardiovascular health over a period of time, rather than an instantaneous measurement like brachial cuff pressure.

Although blood chemistry is the gold standard for screening, diagnosis, and therapy in health wellness and medicine, the prior methods are less than ideal in at least some respects. Currently, a blood panel is requested by a physician and the patient is instructed to travel to a blood laboratory where a phlebotomist can draw blood from the antecubital vein into a series of special collection tubes. The blood is then sent to a central blood chemistry laboratory where it is chemically analyzed using numerous wet chemical assays that have been developed and validated over the years. More recently, a small portion of these tests can be performed in a physician's office using specialized machines employing enzymatic assays. Such delivery of blood to various locations can be less than ideal.

Blood chemistry testing is rapidly moving to the point-of-care (POC) for many reasons. The biggest of these are cost and compliance. Blood testing in the POC and eventually in the home can significantly decrease healthcare costs, can be trackable and reportable, and can be immediate and actionable, sticky, and socially supportive compared to central lab testing. However, current central lab methods often do not translate to the POC and the home, since they often require complicated wet chemistry and expensive instrumentation.

In some cases, blood is often drawn from patients using a lancet. Lancets are small shallow penetration needles or blades designed to pierce skin for the purpose of obtaining capillary blood for a variety of analytical purposes. A lancet generally comprises a sharp tip to pierce skin, a small gauge for painless operation, and a spring-loaded mechanism to propel the cutting surface into tissue and then to allow it to retract. The speed of launch into the tissue and the speed of retraction are both rapid and are designed to minimize pain. Lancets are sterilized and are generally constructed from metal, such as surgical stainless steel. Because of the speed of entry and exit from the skin, the lancet does not usually become coated with blood during the process of lancing.

Once the lancet has penetrated and then retracted from the skin, the lancet is generally removed from the lancing site (which may often be a finger or an arm, but in general could be any place on the surface of the skin). Blood flow from the capillary bed typically begins within a few seconds after lancing. In a typical lancet, the blood that flows from the capillary bed as a result of the lancing procedure is subsequently collected or transferred into a device or container for analysis. For instance, the bead of blood may be allowed to drip from the finger or other lancing site and be collected in a vial or onto a paper card to be sent off to a laboratory for analysis.

In light of the above, it would be desirable to provide improved systems and methods for collecting and analyzing biomarkers obtained from the blood of a patient using a lancet. Ideally, such systems and methods would allow measurements of biomarkers in the blood to be obtained immediately upon collection of the blood. Such systems and methods would obviate the need to send the blood sample obtained by a lancet to a laboratory, instead allowing analysis at the site where the blood sampling was taken.

SUMMARY

Provided herein are methods and systems for collecting and analyzing blood. The methods and systems generally operate by collecting a blood sample on a portion of a lancet and subjecting the blood sample to optical spectroscopy.

In an aspect, a device for collecting and analyzing blood may comprise a lancet having a cutting edge adapted to cut open skin of a subject and a collection area to collect a blood sample from the cut open skin. At least a portion of lancet may be configured to allow light to pass through the blood sample and to direct the light that has passed through the blood sample to an optical spectrometer for subsequent analysis of the blood sample.

The blood sample may be a liquid blood sample and the collection area of the lancet may be configured to allow the liquid blood sample to dry thereon to form a dried blood sample.

At least a portion of the lancet may be optically reflective. At least a portion of the lancet may be constructed from stainless steel. At least a portion of the lancet may be constructed from 316 stainless surgical steel. At least a portion of the lancet may be coated with an optically reflective material.

The lancet may comprise a hollow tube and the cutting edge of the lancet may comprise a beveled tip to the hollow tube. The beveled tip may have a bevel angle in a range from 30 degrees to 45 degrees. The lancet may comprise a needle. The cutting edge of the lancet may be configured to puncture the skin of a subject. The lancet may be configured to remain positioned above the skin subsequent to puncturing the skin, so as to allow the at least the collection area of the lancet to be coated with the liquid blood sample. The lancet may have a distal end having the cutting edge and a proximal end. The lancet may comprise a stop coupled to the proximal end of the lancet to prevent the lancet from puncturing the skin beyond a predetermined length of the lancet. The lancet may comprise a handle coupled to the proximal end of the lancet to allow a user to manipulate the lancet. At least a portion of the handle may be configured to be selectively coupled to a cuvette adapter for the optical spectrometer.

The collection area of the lancet may be configured to collect a sample having a volume less than 10 µL. The collection area of the lancet may be configured to collect a sample having a volume less than 5 µL. The collection area of the lancet may be configured to collect a sample having a volume less than 1 µL.

The optical spectrometer may comprise an infrared spectrometer. The optical spectrometer may comprise a mid-infrared spectrometer. The optical spectrometer may be configured to analyze light in a range of wavelengths from 0.9 µm to 20 µm. The optical spectrometer may be configured to analyze light in a range of wavelengths from 5 µm to 10 µm.

In another aspect, a method of collecting and analyzing blood may comprise: cutting the skin of a subject with a lancet; collecting a blood sample of the subject with the lancet; passing light through the blood sample on the lancet; and collecting the light passed through the blood sample with an optical spectrometer for analysis of the blood sample.

The blood sample may be a liquid blood sample and the method may further comprise allowing the liquid blood sample to dry on the lancet to form a dried blood sample. The method may further comprise subjecting the dried blood sample to optical spectroscopy.

Collecting the blood sample of the subject with the lancet may comprise collecting a volume of less than 10 µL of blood. Collecting the blood sample of the subject with the lancet may comprise collecting a volume of less than 5 µL of blood. Collecting the blood sample of the subject with the lancet may comprise collecting a volume of less than 1 µL of blood.

The method may further comprise subjecting the dried blood sample to infrared spectroscopy. The method may further comprise subjecting the dried blood sample to mid-infrared spectroscopy.

The method may further comprise conducting optical spectroscopy upon a plurality of dried blood samples obtained from a plurality of subjects to obtain a plurality of dried blood spectra. The method may further comprise constructing a model from the plurality of dried blood spectra. The model may be constructed using one or more multivariate least squares methods. The model may be constructed using an augmented classical least squares method. The model may be utilized to allow predictive analysis of blood chemistry of an unknown blood sample.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. For example, embodiments within the scope of the disclosure include various combinations of described features or elements not shown or described in detail. Various other modifications, changes and variations which will be apparent to those skilled in the art may be made in the arrangement, operation and details of the method and apparatus of the present disclosure provided herein without departing from the spirit and scope of the invention as described herein.

Provided herein are methods and systems for collecting and analyzing blood. The methods and systems generally operate by collecting a blood sample on a portion of a lancet and subjecting the blood sample to optical spectroscopy.

The embodiments as disclosed herein may be particularly well suited for performing spectroscopic analysis of red blood cell (RBC), proteins, lipids, and combinations thereof, for example for assessing the risk of cardiovascular diseases. Some exemplary conditions or diseases that may be assessed using the spectroscopic analyses as described herein include blood glucose level, blood pressure (e.g., average systolic blood pressure), lipid level (e.g., total cholesterol, high-density lipoprotein (HDL), low-density lipoprotein (LDL), triglycerides), hemoglobin A1c level (HbA1c), hematocrit (Hb), and inflammation (e.g., plasma fibrinogen). The spectroscopic analysis can be performed without in vitro enzymatic analysis, and without lysing the cells or pretreating samples, for example.

As used herein like characters identify like elements.

As used herein light encompasses electromagnetic energy having at least one wavelength within a range of the electromagnetic spectrum extending from the ultraviolet to the far infrared.

Figure 1:
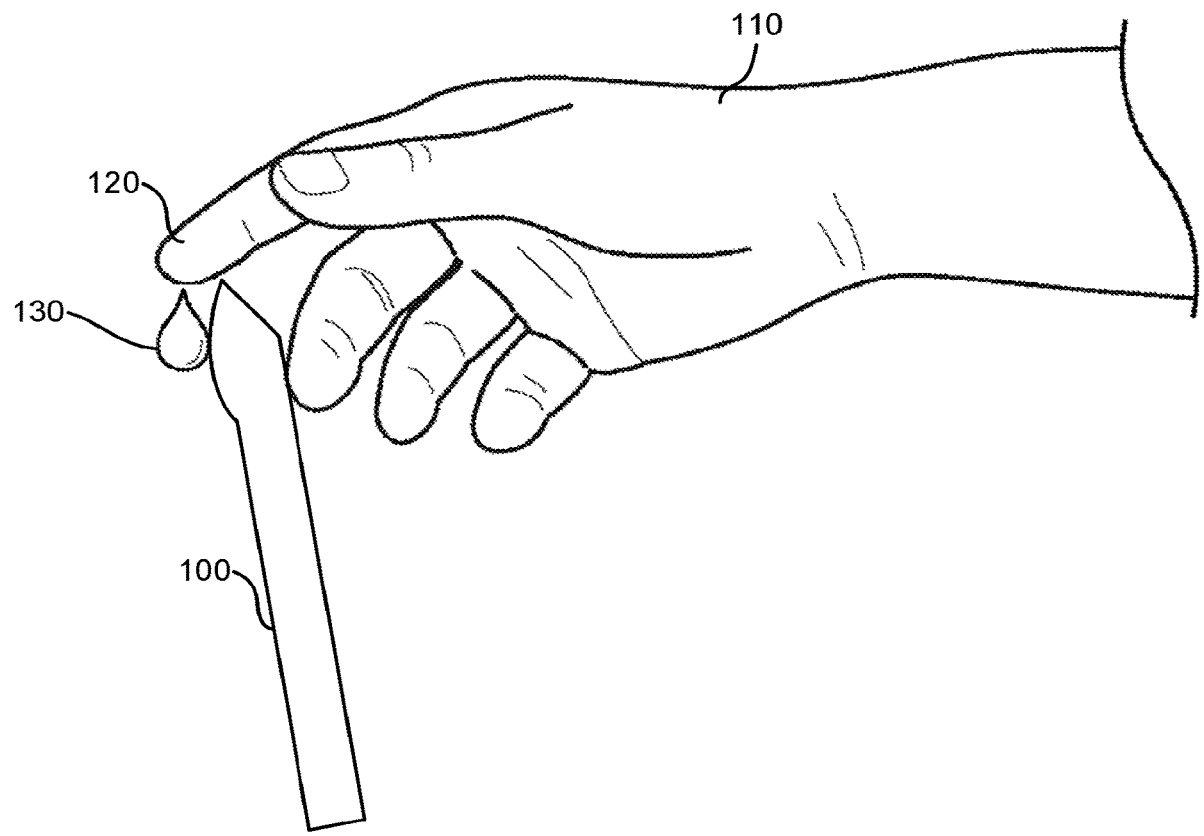
FIG. 1 shows a blood sample from a subject being obtained using a lancet.

FIG. 1 shows a blood sample from a subject being obtained using a lancet. A lancet 100 configured for use with an optical spectrometer, as described herein, may be used to cut a hand 110, such as at a finger 120, to obtain a blood sample 130, as described herein.

The blood sample may comprise red blood cells. The blood sample may comprise white blood cells. The blood sample may comprise serum. The blood sample may comprise plasma.

The blood sample may be analyzed using optical spectroscopy, as described herein.

Although shown as being obtained from a finger of a hand in FIG. 1, the blood sample can be obtained in one or more of many known ways.

Figure 2A:
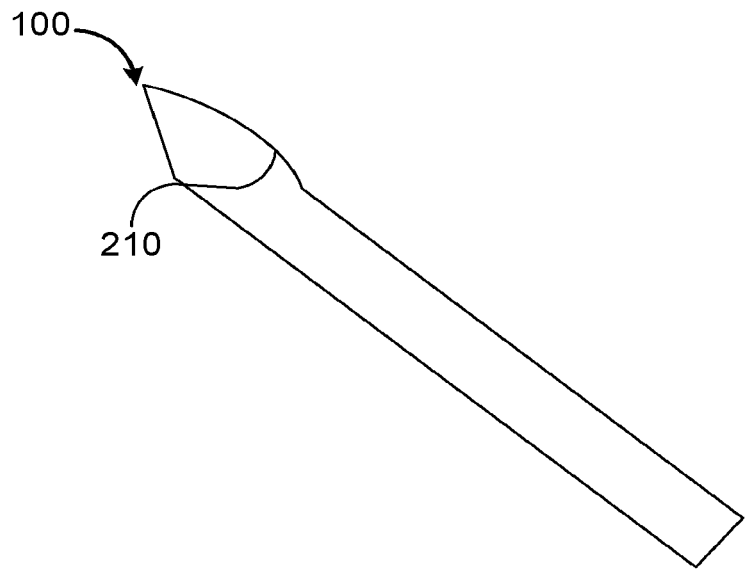
FIG. 2A shows a lancet for use with an optical spectrometer.

FIG. 2A shows a lancet 100 for use with a spectrometer. The lancet may comprise a cutting edge 210. The cutting edge may be adapted to cut open the skin of a subject (such as a human, non-human primate, equine, porcine, murine, canine, feline, or other animal subject). The lancet may be configured to collect a blood sample from the cut open skin of the subject. The lancet may comprise a needle. In such a case, the cutting edge of the lancet may be configured to puncture the skin of the subject and collect a blood sample from the punctured skin of the subject.

The lancet may further comprise a collection area to collect a blood sample from the cut open skin. As shown in FIG. 2A, the cutting edge may comprise the collection area. In some cases, the collection area may be entirely or partially distinct from the cutting edge. The collection area may be configured to receive a liquid blood sample (e.g., liquid blood emanating from the cut open skin). The collection area may be configured to allow the liquid blood sample to dry thereon, forming a dried blood sample on all or a portion of the collection area. The dried blood sample may be subjected to optical spectroscopy, as described herein. Alternatively, the blood sample may be subjected to optical spectroscopy while in a fully hydrated state or a partially hydrated state, as described herein.

The lancet may comprise a hollow tube (not shown). The cutting edge of the lancet may comprise a beveled tip to the hollow tube (not shown). The beveled tip may have a bevel angle of less than 100 degrees, less than 50 degrees, less than 20 degrees, or less than 10 degrees. The beveled tip may have a bevel angle that is within a range defined by any two of the preceding values. For instance, the beveled tip may have a bevel angle that is within a range from 30 degrees to 45 degrees.

All or a portion of the lancet may be constructed from stainless steel, such as 316 stainless surgical steel.

The lancet may comprise a distal end and a proximal end. The distal end may comprise the cutting edge. The proximal end may be opposite the cutting edge. The lancet may comprise a stop (not shown) coupled to the proximal end of the lancet. The stop may prevent the lancet from cutting or puncturing the skin beyond a predetermined length of the lancet. The proximal end may be coupled to a handle (not shown) to allow a user to manipulate the lancet.

The lancet may be configured to remain in a position in close proximity to the blood sample for a period of time sufficient for the blood sample to coat the collection area of the lancet. For instance, the lancet may be configured to remain within a distance of less than 10 mm, less than 5 mm, less than 2 mm, less than 1 mm, less than 0.5 mm, less than 0.2 mm, or less than 0.1 mm away from the blood sample. The lancet may be configured to remain within a distance away from the blood sample that is within a range defined by any two of the preceding values. The lancet may be configured to remain in close proximity to the blood sample for a period of time less than 100 s, less than 50 s, less than 20 s, less than 10 s, less than 5 s, or less than 1 s. The lancet may be configured to remain in close proximity to the blood sample for a period of time that is within a range defined by any two of the preceding values.

The lancet may be configured to collect a sample having a volume less than 100 μL, less than 50 μL, less than 20 μL, less than 10 μL, less than 5 μL, less than 2 μL, or less than 1 μL. The lancet may be configured to collect a sample having a volume that is within a range defined by any two of the preceding values.

To facilitate optical spectroscopy, all or a portion of the lancet may be optically reflective for one or more wavelengths of light in the ultraviolet, visible, near infrared, mid-infrared, or far infrared regions of the electromagnetic spectrum. All or a portion of the lancet may be coated with an optically reflective material (i.e., a material that increases the reflectivity of the lancet for one or more wavelengths of light in the ultraviolet, visible, near infrared, mid-infrared, or far infrared regions of the electromagnetic spectrum). For instance, all or a portion of the lancet may be coated with a metal such as aluminum, silver, or gold, or with one or more dielectric materials, such as magnesium fluoride, silicon dioxide, tantalum pentoxide, zinc sulfide, or titanium dioxide.

Figure 2B:
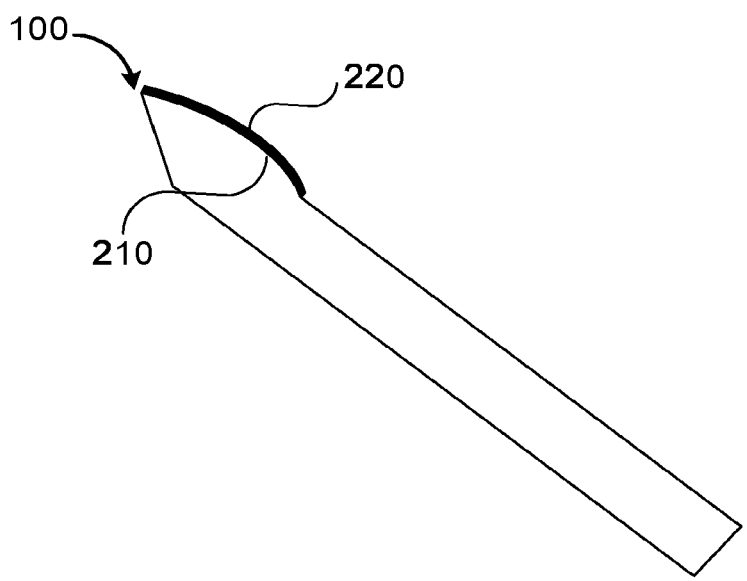
FIG. 2B shows a lancet for use with an optical spectrometer coated with a thin layer of blood.

FIG. 2B shows a lancet 100 for use with a spectrometer coated with a thin layer of blood 220.

Figure 3:
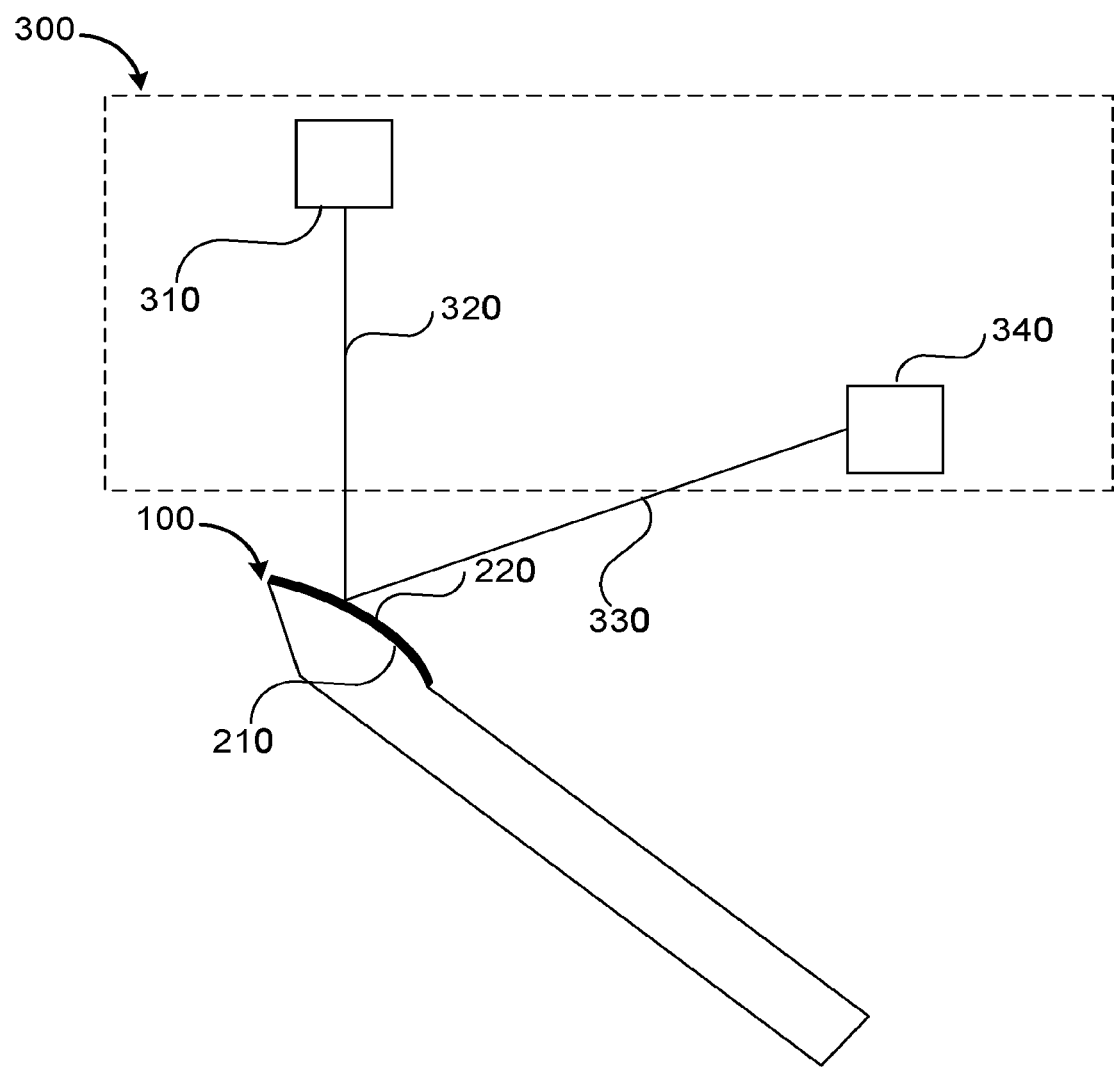
FIG. 3 shows a lancet coated with a thin layer of blood operatively coupled to a spectrometer for spectrometric analysis.

FIG. 3 shows a lancet 100 coated with a thin layer of blood 220 operatively coupled to a spectrometer 300 for spectrometric analysis. The spectrometer may be configured to send light to the blood and receive light from the thin layer of blood. The light may interact with the thin layer of blood, allowing an optical spectrum of the thin layer of blood to be obtained. As shown in FIG. 3, the spectrometer may be a reflectance spectrometer. Alternatively, the spectrometer may be any other known spectrometer.

The spectrometer may comprise one or more light sources 310. The light sources may comprise any known laser or non-laser light source. The light sources may comprise light emitting diodes (LEDs). The light sources may emit first light 320 that may be directed to the thin layer of blood. The first light may comprise one or more wavelengths of light within the ultraviolet, visible, near infrared, mid-infrared, or far infrared regions of the electromagnetic spectrum. The first light may comprise a plurality of wavelengths in a range from 1 μm to 20 μm or a sub-range thereof. The first light may comprise a plurality of wavelengths in a range from 5 μm to 10 μm or a sub-range thereof. The first light may pass through the thin layer of blood, reflect from the lancet, and pass out of the thin layer of blood. During interaction of the first light with the thin layer of blood, one or more wavelengths of the first light may be completely or partially absorbed by the thin layer of blood. Thus, second light 330 having an optical spectrum different than the first light may exit the thin layer of blood. The second light may be directed to one or more optical detectors 340. The detectors may comprise any known optical detectors, such as photodiodes, charge coupled device (CCD) cameras, or complementary metal oxide semiconductor (CMOS) cameras.

The spectrometer 300 may form an optical spectrum based on any known optical spectrometric technique. For instance, the spectrometer may form an optical spectrum based on dispersive or diffractive separation of the second light into its component wavelengths, such as by a prism or grating. Alternatively, the spectrometer may form an optical spectrum by sweeping an emitted wavelength of the light source over time.

Although shown as directing light to the lancet through free space, the optical spectrometer may be coupled to the lancet through other means. For instance, the optical spectrometer may be configured to receive a cuvette. In such case, the lancet may be configured to attachably couple to the cuvette.

Figure 4:
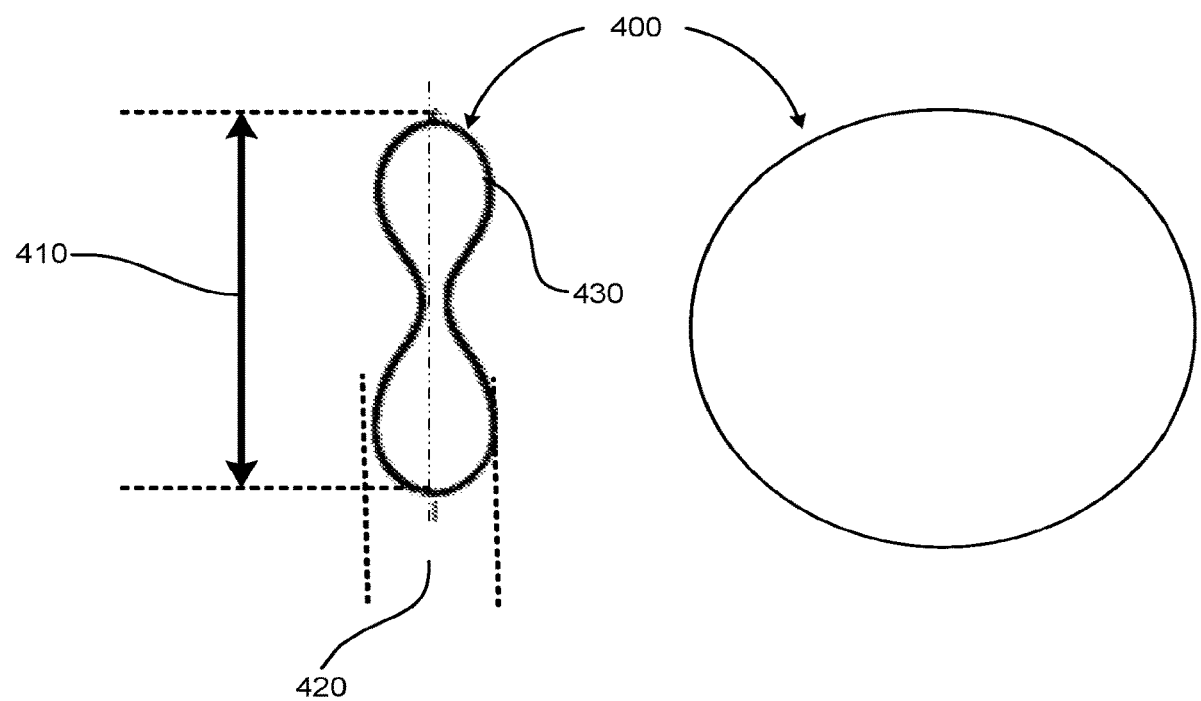
FIG. 4 shows a side profile view and corresponding dimensions of a red blood cell suitable for spectroscopic analysis.

FIG. 4 shows a side profile view and corresponding dimensions of a red blood cell 400 suitable for spectroscopic analysis. The red blood cell may comprise an approximately toroidal shape having a long dimension along an elongate axis defining a length 410 of the red blood cell and a short dimension along a transverse axis defining a thickness 420 of the red blood cell. The length of the red blood cell in the fully hydrated state may be approximately 7 μm and the width may be approximately 2 μm. As described herein, a red blood cell may also be measured in any hydration state, such as a fully hydrated state (about 60% water by weight), a fully dehydrated state (about 0% water by weight), or a partially hydrated or partially dehydrated state (between about 0 to about 60% water by weight). For partially or fully dehydrated red blood cell, the length 410 and/or the thickness 420 of the cell may be smaller than the respective dimensions of the cell in the fully hydrated state.

When the red blood cell is forced through an opening with blood pressure such as an opening of a capillary channel sized smaller than the red blood cell, the shape of the red blood cell may change to allow the red blood cell to pass, and one or more biomarkers such as ATP may be released. Alternatively or in combination, high central blood pressure may result in one or more of deformation of the red blood cell or surface changes to the red blood cell related to the high central blood pressure of the subject, and the biomarkers corresponding to these changes may be measured as described herein.

The optical spectrometers described herein may be configured to measure the membrane 430 of the red blood cells and identify one or more components of the red blood cells specifically.

Figure 5:
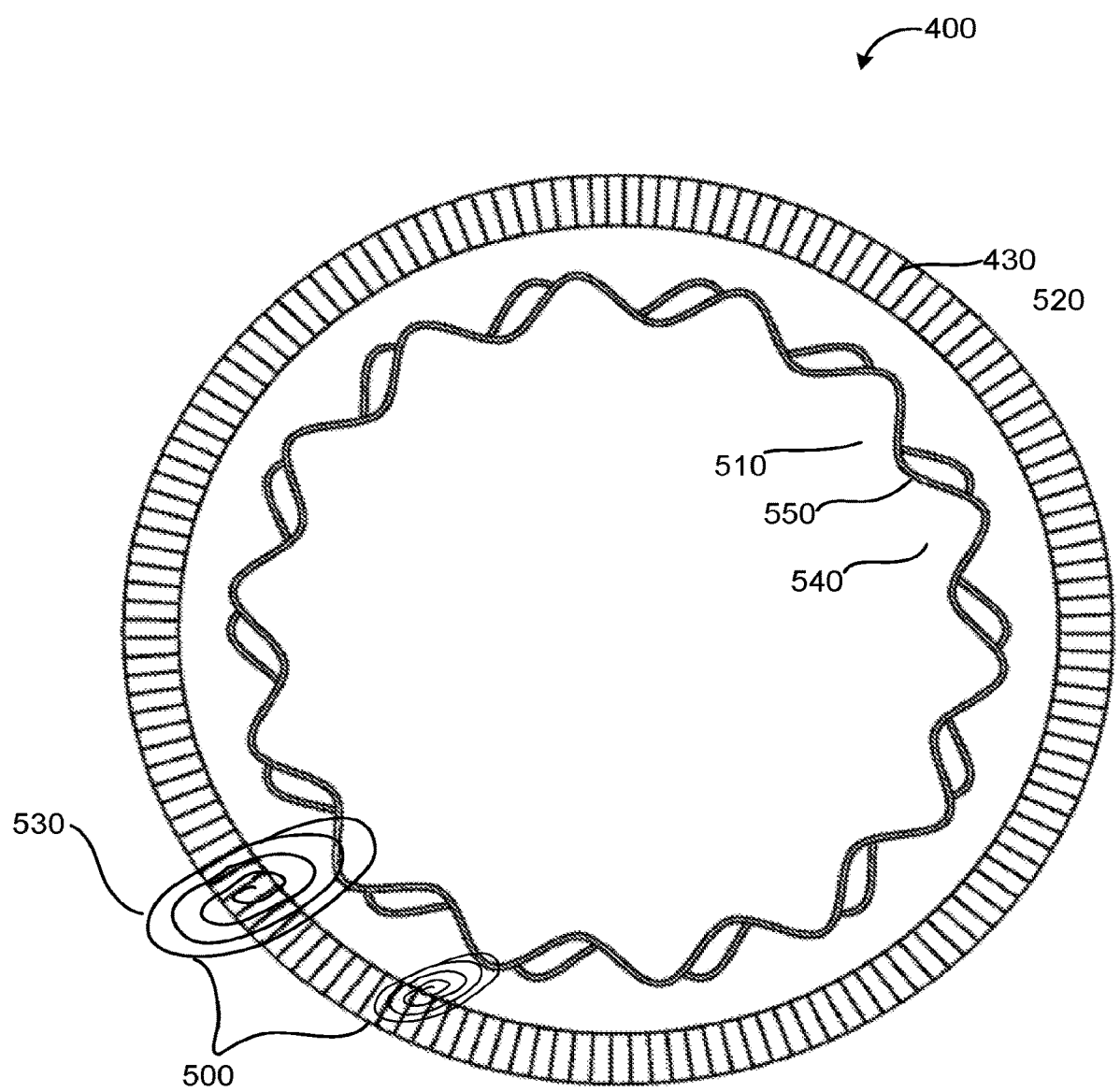
FIG. 5 shows a cross section of a red blood cell.

FIG. 5 shows a cross section of a red blood cell 400. The circular cross section shows structures of the red blood cell membrane 430, membrane proteins 500, and structural proteins 510 within the red blood cell. The circular cross sectional view shows the lipid bi-layer 520 of the red blood cell membrane, which may comprise a phospholipid bi-layer, cholesterol, and phosphatidyl choline, for example. The ratio of components of the lipid bi-layer may be measured using the optical spectrometers described herein. The membrane protein 500 may comprise one or more of many known membrane proteins, such as trans membrane proteins 530. For instance, the membrane protein may comprise one or more of Band 3, Ankyrin, CD47, Rh, or Glycophorin. The red blood cell membrane may comprise a trans-membrane protein such as Ankyrin extending through the membrane in order to transmit ions. The red blood cell membrane may comprise interior proteins such as a spectrin network 540 extending substantially along an interior of the cell membrane and interior to the cell wall.

The red blood cell membrane may correspond to a fluid mosaic model of biological membranes. The membrane may comprise membrane proteins which are mobile within the phospholipid and cholesterol layer. The spectrin network of the membrane skeleton 550 may provide strength to the red blood cell membrane by interacting with the other proteins of the membrane described herein.

Changes in the red blood cell membrane and structures associated with the red blood cell membrane may be measured using the optical spectrometers described herein. For example, lipids levels, changes in lipid levels, lipid ratios, changes in lipid ratios, protein levels, changes in protein levels, protein ratios, changes in protein ratios, protein to lipid ratios, or changes in protein to lipid ratios may be measured.

The measurements may be subjected to an analytical procedure. The analytical procedure may comprise one or more of principal components analysis (PCA) principle components regression (PCR), multivariate curve resolution (MCR), classical least squares (CLS), partial least squares regression (PLS), neural networks, or other bio statistical or chemometric approaches.

Figure 6:
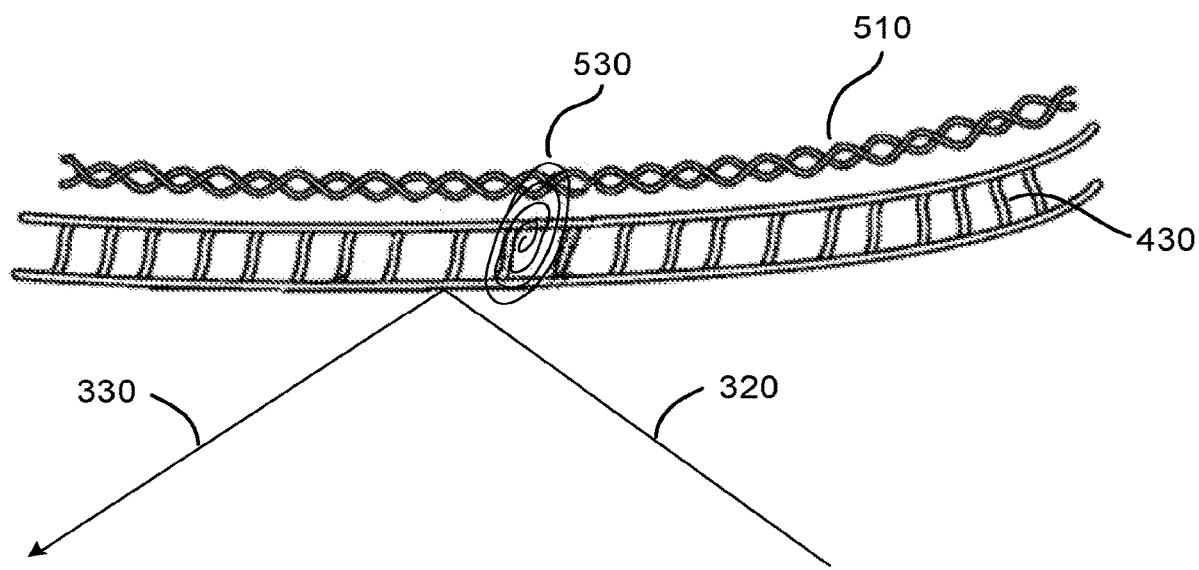
FIG. 6 shows an enlarged view of a red blood cell membrane subjected to spectroscopic analysis.

FIG. 6 shows an enlarged view of a red blood cell membrane 430 subjected to spectroscopic analysis. A measurement light beam 320 transmitted through the red blood cell may interact with components of the red blood cell and be reflected from the lancet to form measurement light 330, as described herein. The measurement light may be indicative of a state of the red blood cell or of a substructure thereof.

The red blood cell may comprise an intact red blood cell as described herein. The red blood cell may comprise a substantially intact red blood cell that is at least partially dried, comprising no more than about 60% water by weight. The red blood cell may comprise a substantially intact red blood cell that is at least partially hydrated, comprising at least about 60% water by weight. The blood sample to be analyzed may comprise red blood cells of a uniform hydration state, or may comprise red blood cells of various hydration states.

Digital Processing Device

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 7:
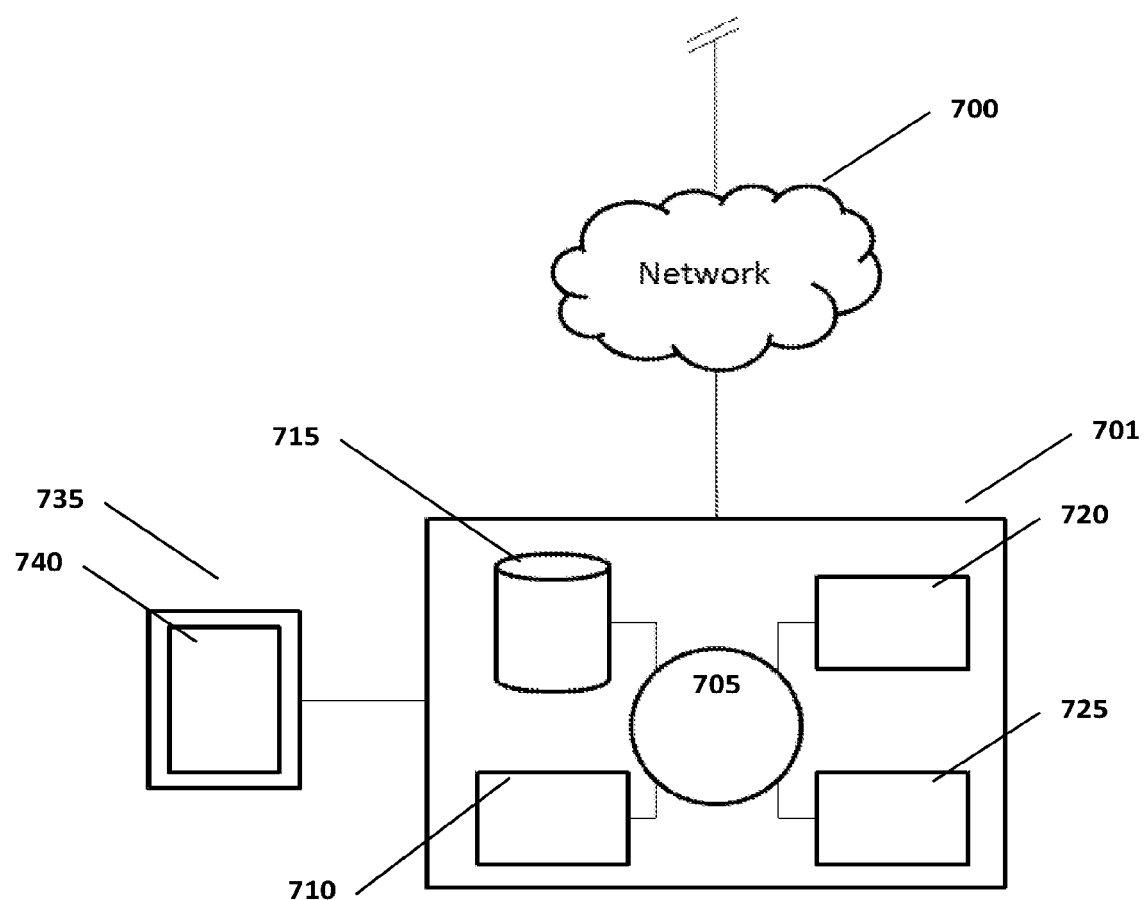
FIG. 7 shows an apparatus comprising a database and a user interface to determine identify markers of red blood cells related to health.

Referring to FIG. 7, in a particular embodiment, an exemplary digital processing device 701 is programmed or otherwise configured to an imaging device as described herein. The device 701 can regulate various aspects of the imaging device of the present disclosure, such as, for example, performing processing steps. In this embodiment, the digital processing device 701 includes a central processing unit (CPU, also "processor" and "computer processor" herein) 705, which can be a single core or multi core processor, or a plurality of processors for parallel processing. The digital processing device 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The digital processing device 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the device 701, can implement a peer-to-peer network, which may enable devices coupled to the device 701 to behave as a client or a server.

Continuing to refer to FIG. 7, the CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and write back. The CPU 705 can be part of a circuit, such as an integrated circuit. One or more other components of the device 701 can be included in the circuit. In some cases, the circuit is an application specific integrated circuit (ASIC) or a field programmable gate array (FPGA).

Continuing to refer to FIG. 7, the storage unit 715 can store files, such as drivers, libraries and saved programs. The storage unit 715 can store user data, e.g., user preferences and user programs. The digital processing device 701 in some cases can include one or more additional data storage units that are external, such as located on a remote server that is in communication through an intranet or the Internet.

Continuing to refer to FIG. 7, the digital processing device 701 can communicate with one or more remote computer systems through the network 730. For instance, the device 701 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 8:
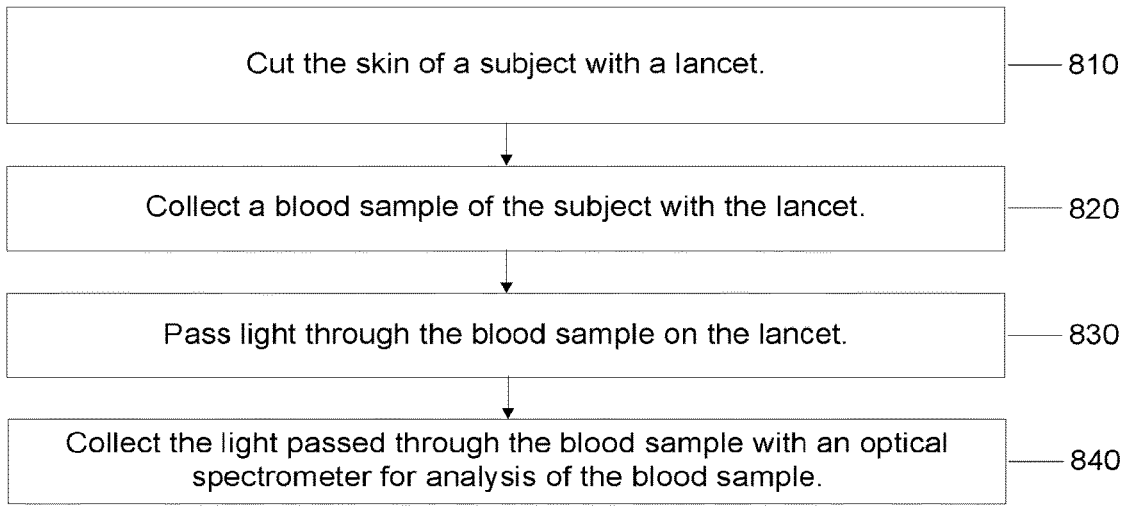
FIG. 8 shows a method for collecting and analyzing blood.

FIG. 8 shows a method 800 for collecting and analyzing blood. The method may comprise operations of: i) cutting the skin of a subject with a lancet; ii) collecting a blood sample of the subject with the lancet; and iii) passing light through the blood sample on the lancet; and iv) collecting the light passed through the blood sample with an optical spectrometer for analysis of the blood sample.

A first operation 810 may comprise cutting the skin of a subject with a lancet. The subject may be any subject described herein. The lancet may be any lancet described herein.

A second operation 820 may comprise collecting a blood sample of the subject with the lancet. The blood sample may be any blood sample described herein. The blood sample may be a liquid blood sample. Collecting the blood sample may comprise collecting a volume of less than 100 µL, less than 50 µL, less than 20 µL, less than 10 µL, less than 5 µL, less than 2 µL, or less than 1 µL of blood. Collecting the blood sample may comprise collecting a volume of blood that is within a range defined by any two of the preceding values. The operation 820 may further comprise allowing the liquid blood sample to dry on the lancet to form a dried blood sample.

A third operation 830 may comprise passing light through the blood sample on the lancet. The light may comprise any light described herein.

A fourth operation 840 may comprise collecting the light passed through the blood sample with an optical spectrometer for analysis of the blood sample. The optical spectrometer may comprise any optical spectrometer described herein. The optical spectrometer may subject the blood sample to any optical spectroscopy described herein, such as infrared spectroscopy or mid-infrared spectroscopy.

The method 800 may be used to conduct optical spectroscopy on a plurality of blood samples obtained from a plurality of subjects to obtain a plurality of blood spectra. The plurality of blood spectra may be used to construct a model. The model may be constructed using one or more methods, such as one or more multivariate least squares methods. For instance, the model may be constructed using an augmented classical least squares method. The model may be any other model described herein. The model may be utilized to allow predictive analysis of blood chemistry of an unknown blood sample.

Ratios of components of the red blood cell or other membranes of another cell may be measured. For example, the ratio of phosphatidyl choline to cholesterol may be measured. The ratios of phospholipids to other components can be measured, such as the ratio of one or more lipid components to a ratio of one or more protein components.

The blood sample may be prepared in one or more of many ways. For instance, the collection area of the lancet, the blood sample, or a solution combined with the blood sample may comprise a clotting antagonist to inhibit blood clotting, in order to allow measurement of red blood cells and to separate the blood cells into a first component having a greater number of red blood cells and a second component having a greater amount of plasma as compared to the sample as drawn from the subject. Alternatively, the blood sample may be allowed to clot such that the sample comprises a first clot component and a second serum component, in which the clotting factors of the plasma have been substantially depleted to form the blood clot.

In some cases, components of the serum or plasma may be measured. In some instances, the plasma and blood cells may be separated at least partially so as to provide different measurements for each component of the blood.

Spectra may be measured from the sample and statistical analysis methods can be used to generate a plurality of factors. The plurality of factors may comprise a plurality of functions upon which the data may be projected in order to determine the amount, or concentration, of each function in the sample. The factors may be orthogonal or non-orthogonal, for example. The analysis can comprise one or more of principle components analysis (PCA), principle components regression (PCR), classical least squares (CLS), multivariate curve resolution (MCR), partial least squares regression (PLS), neural networks, or other biostatistical or chemometric approaches, for example. The factors may be orthogonal to each other. Alternatively, at least some of the factors may comprise non-orthogonal factors. One or more relevant factors may be identified, and the red blood cell status or history may be determined in response to the one or more relevant factors. The history of the red blood cells may comprise a control of the red blood cells of the subject, such as a control of a condition such as high blood pressure of the subject. The one or more relevant factors may comprise one or more statistically relevant factors, for example.

A plurality of spectral bands may comprise peaks related to structures of the cell such as protein structure of the red blood cell. The Amide I band of frequencies comprising the Amide I peak may correspond to alpha helix protein structures of the proteins of the red blood cell membrane. The Amide II band of frequencies comprising the Amide II peak may correspond to beta-sheet protein structures of the cell membrane. The band of frequencies comprising the Amide III band may correspond to disordered protein structures of the cell membrane. The determination of factors corresponding to these spectral bands and the shifts of peaks and intensities of these spectral bands in response to the measure spectra can be used to determine the one or more biomarkers of the cellular membrane such as the red blood cell membrane.

Deformation of the red blood cell membrane may result in measurable spectroscopic changes to the red blood cell membrane that may be measured as described herein. The measurable changes may comprise shifts in the spectral peaks as disclosed herein. The spectroscopic changes to the red blood cell membrane may be substantially instantaneous, such as upon deformation of the red blood cell membrane. Alternatively, the spectroscopic changes to the red blood cell membrane may comprise changes occurring over the history of the red blood cell, such as over a long term three month history corresponding to the functional lifetime of the red blood cell.

The factors may be used to determine the history of the red blood cell, and may be used to determine the long term control of a condition such as hypertension, for example. The long term control may comprise a conformational change to the red blood cell membrane that can be determined with at least one factor as disclosed herein, such as with a relationship among factors as disclosed herein.

A substance related to the health status of the subject may not itself be detectable with the spectral measurements described herein. The measurement of the red blood cell membrane can provide, however, an optical spectral signal to determine the presence of the substance. For example, spectral changes of the red blood cell membrane provided with aspirin as disclosed herein can be used to identify a response of the red blood cell membrane to aspirin, even though the presence of aspirin itself may not be detectable spectroscopically in some embodiments. The optical waveguide can be configured to provide a plurality of reflections from the evanescent wave measurement surface in order to provide an increased amplification of the measured evanescent wave signal.

The operations of the method 800 are provided as an example of a method of measuring a sample, in accordance with embodiments. A person of ordinary skill in the art will recognize many variations and modifications based on the disclosure provided herein. For example, some operations may be added or removed. Some of the operations may comprise sub-operations, and many of the operations may be repeated. The processor as described herein may be programmed with one or more instructions to perform one or more of the operations of method 800.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

EXAMPLES

Example 1: Optical Spectroscopy of Blood Collected on a Lancet

Figure 9:
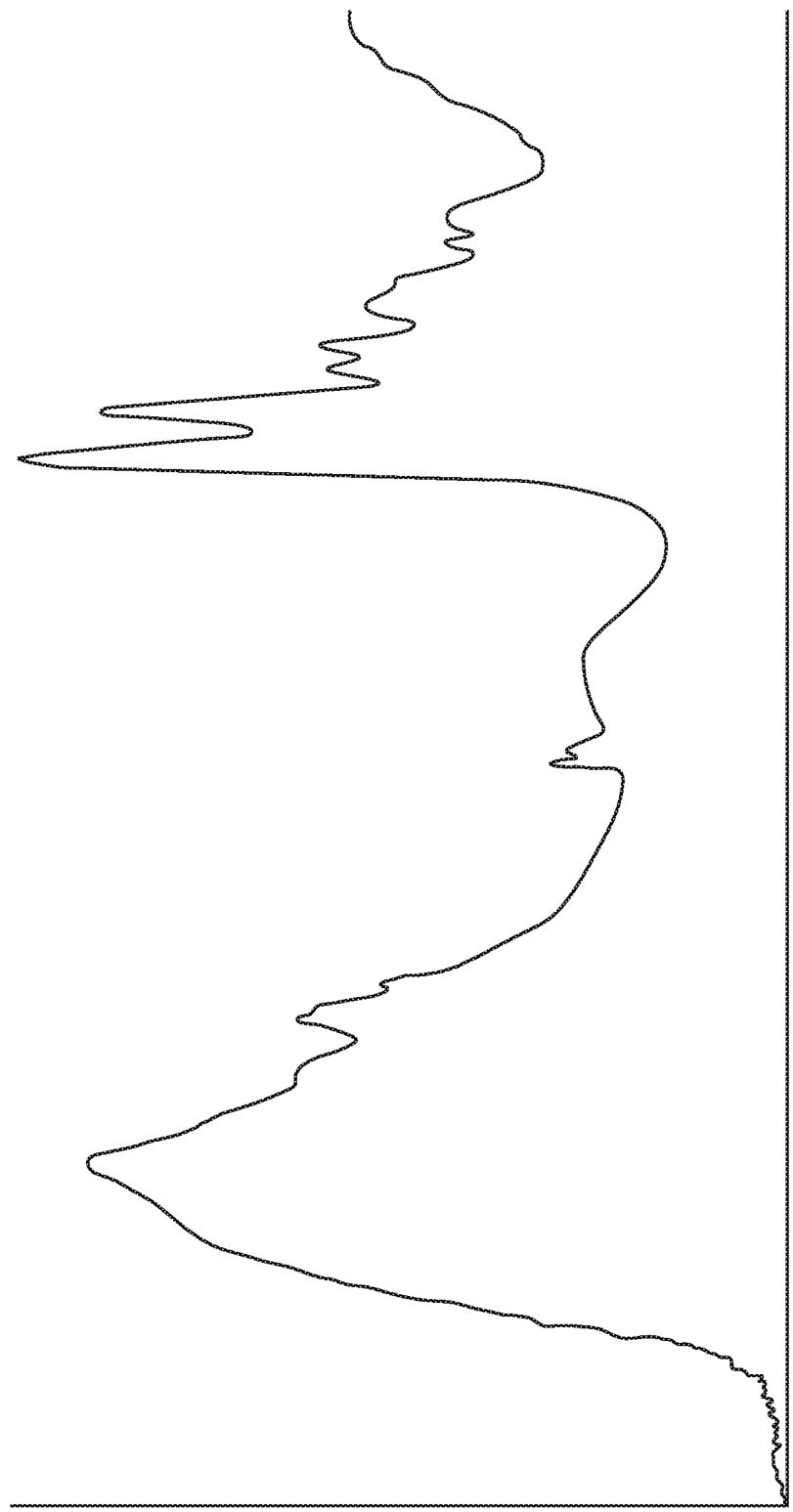
FIG. 9 shows an example mid-infrared spectrum of blood collected on a lancet.

FIG. 9 shows an example mid-infrared spectrum of blood collected on a lancet.

I claim:

1. A method of collecting and analyzing blood, said method comprising:
   cutting a skin of a subject with an optically reflective portion of a lancet;
   collecting a liquid blood sample of the subject with the optically reflective portion of the lancet;
   allowing the liquid blood sample to dry on the optically reflective portion of the lancet to form a dried blood sample;
   passing light through the dried blood sample on the lancet; and
   subjecting the dried blood sample to an optical spectroscopy by collecting the light passed through the dried blood sample and reflected off of the optically reflective portion of the lancet with an optical spectrometer for analysis of the blood sample.

2. The method of claim 1, wherein collecting the blood sample of the subject with the lancet comprises collecting a volume of less than 10 μL of blood.

3. The method of claim 1, wherein collecting the blood sample of the subject with the lancet comprises collecting a volume of less than 5 μL of blood.

4. The method of claim 1, wherein collecting the blood sample of the subject with the lancet comprises collecting a volume of less than 1 μL of blood.

5. The method of claim 1, wherein the optical spectroscopy comprises infrared spectroscopy.

6. The method of claim 1, wherein the optical spectroscopy comprises mid-infrared spectroscopy.

7. The method of claim 1, further comprising conducting optical spectroscopy upon a plurality of dried blood samples obtained from a plurality of subjects to obtain a plurality of dried blood spectra.

8. The method of claim 7, further comprising constructing a model from the plurality of dried blood spectra.

9. The method of claim 8, wherein the model is constructed using one or more multivariate least squares methods.

10. The method of claim 8, wherein the model is constructed using an augmented classical least squares method.

11. The method of claim 8, further comprising utilizing the model to allow predictive analysis of blood chemistry of an unknown blood sample.

12. The method of claim 1, wherein the optically reflective portion of the lancet comprises a beveled tip.

13. The method of claim 12, wherein the beveled tip comprises a bevel angle of less than 100 degrees.

14. The method of claim 12, wherein the beveled tip comprises a bevel angle of less than 50 degrees.

15. The method of claim 12, wherein the beveled tip comprises a bevel angle of less than 20 degrees.

16. The method of claim 12, wherein the beveled tip comprises a bevel angle of less than 10 degrees.

* * * * *